(12) United States Patent
Merz et al.

(10) Patent No.: US 10,251,632 B2
(45) Date of Patent: Apr. 9, 2019

(54) SURGICAL INSTRUMENT, HANDLE, OPERATING METHOD, AND METHOD FOR DISMANTLING SAME

(71) Applicant: Karl Storz GmbH & Co. KG, Tuttlingen (DE)

(72) Inventors: Robin Merz, Furtwangen (DE); Jochen Stefan, Wald (DE)

(73) Assignee: Karl Storz SE & Co. KG, Tuttlingen (DE)

(*) Notice: Subject to any disclaimer, the term of this patent is extended or adjusted under 35 U.S.C. 154(b) by 987 days.

(21) Appl. No.: 14/618,423

(22) Filed: Feb. 10, 2015

(65) Prior Publication Data

US 2015/0257742 A1 Sep. 17, 2015

(30) Foreign Application Priority Data

Feb. 10, 2014 (DE) .................. 10 2014 101 603

(51) Int. Cl.
*A61B 17/00* (2006.01)
*A61B 17/29* (2006.01)
(Continued)

(52) U.S. Cl.
CPC ........ *A61B 17/00* (2013.01); *A61B 17/00234* (2013.01); *A61B 17/0218* (2013.01); *A61B 17/221* (2013.01); *A61B 17/2909* (2013.01); *A61B 17/3201* (2013.01); *A61B 2017/0046* (2013.01); *A61B 2017/00371* (2013.01); *A61B 2017/00424* (2013.01); *A61B 2017/00429* (2013.01); *A61B 2017/00433* (2013.01); *A61B 2017/00469* (2013.01);
(Continued)

(58) Field of Classification Search
CPC .............. A61B 17/00; A61B 17/00234; A61B 17/0218; A61B 17/221; A61B 17/2909; A61B 17/3201
USPC ........................................................... 606/1
See application file for complete search history.

(56) References Cited

U.S. PATENT DOCUMENTS 4,691,705 A * 9/1987 Okada .................. A61B 17/221
606/127
2002/0026202 A1 2/2002 Honey et al.
(Continued)

FOREIGN PATENT DOCUMENTS

DE 19920869 A1 12/2000
EP 2535009 A2 12/2012
(Continued)

*Primary Examiner* — Gary Jackson
*Assistant Examiner* — Sebastian X Lukjan
(74) *Attorney, Agent, or Firm* — Whitmyer IP Group LLC (57) ABSTRACT

A handle for a surgical instrument, which handle has a carriage designed to move an actuation rod. A second actuation element is arranged adjacent to the first actuation element and is rotatable over the longitudinal axis of the main body. The second actuation element is annular, toward the first actuation element, and carries on its inner circumference a rotationally fixed locking ring. The carriage has a finger which extends, eccentrically with respect to the longitudinal axis of the main body, from a front face of the carriage facing the locking ring. In a locked state, a protuberance on the ring provides an abutment for the carriage. In the release state, the finger is offset with respect to the protuberance, and a range of travel of the carriage is freed.

19 Claims, 6 Drawing Sheets

(51) Int. Cl.
  *A61B 17/02* (2006.01)
  *A61B 17/3201* (2006.01)
  *A61B 17/221* (2006.01)
  *A61B 90/00* (2016.01)

(52) U.S. Cl.
  CPC . *A61B 2017/292* (2013.01); *A61B 2017/2912* (2013.01); *A61B 2090/034* (2016.02); *A61B 2090/0813* (2016.02); *Y10T 29/49815* (2015.01)

(56) References Cited

U.S. PATENT DOCUMENTS

2003/0009176 A1    1/2003  Bilitz
2012/0088972 A1*   4/2012  Pinkowski ........... A61B 17/221
                                                           600/131

FOREIGN PATENT DOCUMENTS

WO       9204059 A1    3/1992
WO       0064357 A1   11/2000

* cited by examiner

SURGICAL INSTRUMENT, HANDLE, OPERATING METHOD, AND METHOD FOR DISMANTLING SAME

FIELD OF THE INVENTION

The following invention relates to a handle for a surgical instrument, the surgical instrument itself, a method for operating it, and a method for dismantling the instrument.

BACKGROUND OF THE INVENTION

Surgical instruments for use in minimally invasive surgery, such as scissors, forceps, needle holders and other grippers and retractors, are known. The actual tool or the tool head is arranged on a distal end of a shaft, wherein the actuation is effected by an actuation grip which is arranged at the proximal end and which is operatively coupled to the tool head by an actuation rod or a cable pull. The actuation rod can be actuated via a rotary wheel, which is coupled to a movable carriage, for example, via a movement thread. With the rotary wheel, however, only one function of the tool head can be controlled, namely the opening and closing thereof within predetermined limits.

In order to be better able to clean the surgical instrument and to be able to use an actuation grip with different tool heads, it is moreover known that the shaft can be uncoupled. For this purpose, locking means are mounted on a distal coupling portion of the actuation grip and on the movable drive carriage, which locking means can be actuated separately from each other from the outside, such that two hands are always needed to release them.

SUMMARY OF THE INVENTION

Proceeding from this prior art, the object of the present invention is to make available an improved handle for a surgical instrument, which handle is able to control an additional function of a tool head and can be uncoupled from a shaft more ergonomically than before.

This object is achieved by a handle for an instrument, a surgical instrument, and/or an operating method according to the invention.

There is also the object of making available a surgical instrument that can be operated more ergonomically than known surgical instruments and that can be easily dismantled.

Preferred developments of the devices are described by the dependent claims respectively.

A further object of the invention is to make available an operating method for a surgical instrument according to the invention, which method allows the additional function of the tool head to be controlled in an ergonomic and reliable way.

Finally, there is also the object of making available a dismantling method for the surgical instrument according to the invention, which method allows the instrument to be dismantled more ergonomically and more quickly.

In a first embodiment, the handle according to the invention for a surgical instrument comprises a distal coupling portion for coupling to a shaft, in the present case always an instrument shaft. The handle moreover comprises an elongate main body, in which a carriage is guided movably along the longitudinal axis between a first end position and a second end position. Here, elongate means substantially cylindrical, wherein the top surfaces of the cylinder, which can be a cylinder with a round, oval or polygonal cross section, do not necessarily have to be perpendicular to the longitudinal axis, in this case it is more a tubular main body. In both cases, the main body can have entirely hollow and solid longitudinal axis portions. The handle has an actuation element, which is operatively coupled to the carriage in order to generate the axial movement. The carriage is intended to move an actuation rod of a shaft of the surgical instrument. The handle moreover has a second actuation element which is arranged on the main body adjacent to the first actuation element on the longitudinal axis, wherein the second actuation element is arranged to be rotatable about the longitudinal axis of the main body and over the latter. In addition, the second actuation element is annular, at least at its end directed toward the first actuation element, and at this end carries on its inner circumference a locking ring, which is fixed in rotation with respect to the second actuation element. An inner wall of the locking ring has a protuberance facing radially into the locking ring, said protuberance having a surface lying at least partially in the ring plane. The carriage has a finger which extends, eccentrically with respect to the longitudinal axis of the main body, from a front face of the carriage facing the locking ring. In a locked state of the second actuation element, the surface of the protuberance of the locking ring provides a first abutment for the carriage, since the finger comes to bear on the surface. By contrast, in a release state of the second actuation element, the finger is offset with respect to the surface of the protuberance of the locking ring and frees a range of travel for the carriage.

The first actuation element can in particular be a rotary wheel or a lever, which can be guided preferably coaxially on the main body. The surface of the protuberance of the locking ring can lie completely in the ring plane, and it is also possible that the surface is oriented at an angle to the ring plane, such that only an imaginary line of intersection lies in the ring plane. The coupling portion does not have to be arranged at the very outer distal end of the handle and instead can be present in a distal end portion, which end portion can have a length corresponding to half the total length of the handle.

The range of travel freed by rotation of the second actuation element is not required during normal operation of the handle. Rather, by moving the carriage along the additional range of travel, a seldom required function of a surgical tool operatively coupled to the handle can be used. Thus, forceps or scissors can in this way be brought to what is, for example, a beyond open position. To ensure that the beyond open position is not reached inadvertently, the deliberate actuation of the second actuation element is first of all needed. Advantageously, provision can be made that the angle positions of the second actuation element, which correspond to the locked state and release state, are predetermined by suitable abutments, such that the locked position can be reached simply by rotation in one direction and the release position can be reached simply by rotation in the respective other direction, without having to pay attention to the angle by which the second actuation element is rotated. The protuberance itself can serve as angular abutment, in which case only a mating abutment of the main body has to be created corresponding to the release position and the locked position. Depending on the field of use of the handle, the second actuation element can be arranged either proximally or distally from the first actuation element, wherein a distal arrangement is advantageous since the first actuation element is used more frequently than the second actuation element, the latter being provided only to control the "additional function". However, the inventive concept concerning the interaction of the eccentric finger of the carriage with the rotatable protuberance of the locking ring can also be easily implemented if the second actuation element is arranged proximally from the first actuation element.

In a further embodiment, the second actuation element can be movable along a longitudinal axial portion of the main body. This degree of freedom of movement of the second actuation element can be used to operate a function of the handle or a function of a surgical tool operatively coupled to the handle.

In a further embodiment, the main body can have, on its outer circumference, a lug which is positioned such that, in the locked state of the second actuation element, it bears on the surface of the protuberance of the locking ring whereas, in the release state of the second actuation element, the lug is offset with respect to the protuberance. Alternatively or in addition, the protuberance can also be beveled in the circumferential direction of the locking ring.

Since the dimensions of the lug and of the protuberance of the locking ring are matched to each other, the degree of freedom of movement along the longitudinal axis of the main body can be blocked in the locked state of the second actuation element, and it can be freed, when necessary, by the second actuation element being brought to the release state. In order to perform the function assigned to the longitudinal axial movement of the second actuation element, the second actuation element first of all has to be rotated to the release state. Only in the release state of the second actuation element can the locking ring be guided over the lug together with the second actuation element. A beveled design of the locking ring is advantageous since the locking ring can then also be rotated with little force, if the finger of the carriage is pressed onto it, for example by strong actuation of the first actuation element. Also in the interaction of the lug of the main body with the finger of the carriage, it has to be ensured that the second actuation element can be moved along the longitudinal axis with the locking ring in its release state, such that finger and lug can pass together through the ring plane. For this purpose, the dimensions and the positioning of the finger and of the lug together must be matched to the protuberance of the locking ring.

The lug can in particular have a hook-shaped cross section that can advantageously extend substantially along the outer circumference of the main body, wherein a transition of the main body to the hook-shaped contour of the lug can preferably be made tangentially. In addition, the lug can also extend along a portion parallel to the longitudinal axis of the main body. The lug nestles on the main body, more or less as a continuation of the cross section of the main body, and protrudes no further radially outward than the main body itself, as a result of which the second actuation element can also be easily moved over the lug.

Moreover, the carriage can have a coupling device, preferably a locking device, in particular a locking slide, most preferably a spring-loaded locking slide, wherein the actuation rod of the shaft can be coupled releasably to the coupling device of the carriage. In addition, the main body can also have a coupling device, preferably a locking device, preferably a locking slide, most preferably a spring-loaded locking slide, wherein this coupling device can be coupled releasably to the jacket tube of the shaft. In addition to the last-mentioned coupling devices, other coupling devices may also be suitable; in any case, the invention is not thereby limited. The locking slides can each be connected to an actuation pin, by way of which an actuating force can be applied to the slides. For this purpose, the respective actuation pin can extend in particular over the one outer contour of the carriage or of the main body at the longitudinal axial position of the locking slide.

Moreover, the second actuation element can be operatively coupled to a trigger device, which extends parallel to the longitudinal axis of the main body. The trigger device is operatively connected to the coupling device of the main body and of the slide and, in the release state of the second actuation element, can be moved along the longitudinal axis together with the second actuation element to a trigger position.

In this embodiment, the degree of freedom of longitudinal axial travel of the second actuation element means that a shaft that is coupled to the handle can also be uncoupled again. In contrast to known handles in which two spatially separate locks always have to be actuated, according to the present invention both locks, the one for the actuation rod and the one for the jacket tube of the shaft, are triggered by a common trigger device. It is also advantageous that the trigger device of the present invention cannot be inadvertently actuated, since the degree of freedom of longitudinal axial movement of the second actuation element is activated only in the release state of the second actuation element. In addition to improved ergonomics when uncoupling the shaft, the handle according to the invention affords a high level of security against incorrect operation.

According to a further embodiment, the trigger device can have a first part, which is movable together with the second actuation element, and a second part, which is stationary with respect to the longitudinal axis of the main body. The first part and/or the second part of the trigger device preferably comprise(s) a trigger band which, in one or more portions, has wedge-shaped, undulating or beveled portions in longitudinal section. The wedge-shaped, undulating or beveled portions each contact a trigger rib of the respective other part.

Here, stationary with respect to the longitudinal axis of the main body means that a movement of the corresponding part of the trigger device parallel to the longitudinal axis is blocked, while a movement in other directions, in particular perpendicular to the longitudinal axis, is possible. Upon actuation of the degree of freedom of longitudinal axial movement of the second actuation element, the respective wedge-shaped, undulating or beveled portion slides down on the corresponding trigger rib of the other part, as a result of which a lifting movement of the trigger device is generated in a direction perpendicular to the direction of travel. This lifting movement is transmitted to the coupling device of the carriage and of the main body, as a result of which the engagement of the jacket tube and of the actuation rod of the shaft with the coupling devices is canceled. The trigger band with the wedge-shaped, undulating or beveled portions can be the entrained part or the stationary part. Provision can even be made that one of the two parts is an integral component of the main body; for example, the trigger ribs can be formed integrally on the main body.

Furthermore, a resetting device can be arranged between the second actuation element and the main body, in particular a spring, which is intended to reset the second actuation element.

The rest position, to which the second actuation element is reset, is advantageously the longitudinal axial position in which the ring plane of the locking ring points to a front face of the lug facing the locking ring, i.e. a position in which the trigger device is unactuated. This constitutes additional protection against incorrect operation of the trigger device. Moreover, the second actuation element is always brought by the resetting device to a longitudinal axial position in which a shaft can once again be coupled after the uncoupling.

Moreover, the main body can have a longitudinal axial guide groove in which the carriage is guided. When the carriage is located at its first abutment, there is a distance between the front face of the carriage facing the locking ring and an opposite end of the guide groove, the length of which distance is at least as great as half the length of the finger. It is thereby made possible that the range of travel of the carriage additionally freed by rotation of the locking ring is limited. In this embodiment, the actuation band of the trigger device can extend along the bottom of the groove, wherein a lifting movement can be achieved that is uniform along the entire length of the groove, since in the wedge-shaped, undulating or beveled portions uniform distance with corresponding trigger buttons are provided. A coupling device arranged on the carriage can thus be released independently of an actual longitudinal axial position of the carriage.

Alternatively or in addition, in an area of the cylindrical main body, a segment can be recessed in which the guide groove is present. The recessed segment forms a kind of rail or a sliding surface for the carriage, wherein the carriage can have a T-shaped cross section or with a mushroom cross section. In order to further improve the ergonomic properties, in particular to improve the force feedback, the sliding surface can be provided with a slide-promoting coating or surface structuring. The recessed segment of the cylindrical main body can advantageously extend in the direction of the second actuation element to a point behind the locking ring in the "rest position" of the second actuation element, since the rotation of the second rotation element can be limited by interaction of the protuberance of the locking ring and the plane sliding surface of the recessed segment, because the protuberance bears on the plane sliding surface and the second actuation element cannot be rotated further. In the area of the recessed segment, the cross section of the cylindrical main body is limited outwardly by an arc of a circle and a chord, such that the recessed segment could almost be referred to as a "flattened part" in the longitudinal axial direction.

Concentrically within the second actuation element, a guide sleeve can be arranged stationary with respect to the main body and, at least at an angle position corresponding to the locked state of the second actuation element, has a longitudinal axial guide track in which a corresponding engagement means of the second actuation element or of the locking ring is guided.

By interaction with the corresponding engagement means of the second actuation element and of the locking ring, the guide track of the guide sleeve ensures that the second actuation element cannot be inadvertently rotated during the longitudinal axial movement to actuate the trigger device. In this way, the second actuation element can be moved along the longitudinal axis without the user having to take care to hold it in the rotation position.

The first actuation element can in particular be a rotary wheel, which is coupled to the carriage via a movement thread or a slotted guide, for example. To generate the axial movement of the carriage, the rotary wheel is arranged in a fixed position with respect to the longitudinal axis of the main body. On its inner circumferential surface, it can have a movement thread which engages with a corresponding movement thread portion of the carriage. By way of a slotted guide, a nonlinear transmission ratio between the rotation movement of the rotary wheel and the axial movement of the carriage can be achieved, which can be used to influence the force feedback properties, in particular to compensate for a nonlinear transmission ratio of a tool operatively coupled to the handle.

In a first embodiment, the surgical instrument according to the invention has a handle to which is coupled a shaft in which an actuation rod is guided movably along the longitudinal axis, which actuation rod is coupled to a longitudinally axially movable carriage of the handle. A tool head is coupled to a distal end of the shaft and can be transferred by means of the actuation rod from an open state to a closed state. The handle is a handle according to the invention as disclosed herein.

The tool head can carry a cutting tool, for example scissors, or a gripping tool, for example a clamp, a needle holder, forceps or a retaining tool such as a retractor (e.g. a ring retractor or surface retractor). Such tools are usually brought to the closed state by pulling back the actuation rod and are brought to the open state by pushing the actuation rod to the distal end. In previously known surgical instruments, the angle range of the tool lying between the open state and the closed state is predetermined by two abutment positions. By contrast, when using the handle according to the invention, it is possible, in addition to the two abutment positions used in normal operation, to achieve a further functional position of the tool by moving the carriage through the additional range of travel, as a result of which the tool can be brought to a beyond open position. The beyond open position is only seldom needed, but it is helpful when cleaning and/or dismantling the surgical instrument, since the handle can be locked in this position, as a result of which the cleaning and/or dismantling can be carried out more conveniently and more reliably than in known surgical instruments.

In a further embodiment of the surgical instrument, the shaft can have a jacket tube which is preferably coupled, in particular releasably, to the distal coupling portion of the handle. The jacket tube particularly preferably has a locking means, in particular a locking indent or a circumferential locking groove, which is in engagement with the coupling device of the main body. Alternatively or in addition, the actuation rod can also have a locking means, preferably a locking indent or a circumferential locking groove, which is in engagement with the coupling device of the carriage.

The operating method for a surgical instrument allows the tool head of a surgical instrument according to the invention to be transferred to a beyond open position. The following steps are carried out:
  rotating the second actuation element of the handle until the protuberance of the locking ring and the finger of the carriage are offset with respect to each other, thereby transferring the second actuation element to the release state,
  thereby releasing the range of travel of the carriage,
  actuating the first actuation element, thereby moving the carriage in the direction of the locking ring and moving the finger as far as an end position behind the ring plane, and thereby indirectly transferring the tool head to the over-open position.

If the method is carried out with an embodiment of the surgical instrument whose main body has the segment-shaped recess, the end angle of the rotation of the second actuation element is advantageously predefined by the abutment of the protuberance of the locking ring on the sliding surface. The release position and the locked position can also be obtained "blind"; the method can be carried out intuitively without a long training period. Moreover, the method is also fail-safe, since the range of travel of the carriage is freed only after active intervention on the part of the user, namely the rotation of the second actuation element.

Finally, the dismantling method according to the invention for a surgical instrument according to the invention comprises the following steps:

rotating the second actuation element of the handle until the protuberance of the locking ring and the lug are offset with respect to each other, thereby transferring the second actuation element to the release state, thereby freeing a passage of the locking ring for the lug of the main body of the handle, moving the second actuation element in a direction toward the locking abutment, thereby entraining the trigger device and bringing it to the trigger position, thus generating a lifting movement of the trigger device in a direction perpendicular to the direction of movement of the second actuation element, transmitting the lifting movement of the trigger device to the coupling devices of the carriage and of the main body, thereby actuating the coupling devices and releasing the engagement of the locking means of the jacket tube of the shaft with the coupling device of the main body and of the locking means of the actuation rod of the shaft with the coupling device of the carriage, jointly separating the jacket tube and the actuation rod from the handle.

The dismantling method can be carried out very ergonomically since both locking means, namely that of the jacket tube and that of the actuation rod, are triggered simultaneously by longitudinal axial movement of the second actuation device. Only one hand is needed for this, so that the other hand remains free for holding the handle or for detaching the instrument shaft.

These and further advantages are set forth in the following description with reference to the accompanying figures. The reference to the figures in the description is for assisting with the description and for easier understanding of the subject matter. Items or parts of items that are substantially equal or similar can be provided with the same reference signs. The figures are merely schematic depictions of illustrative embodiments of the invention.

DETAILED DESCRIPTION OF THE INVENTION

Figure 1A:
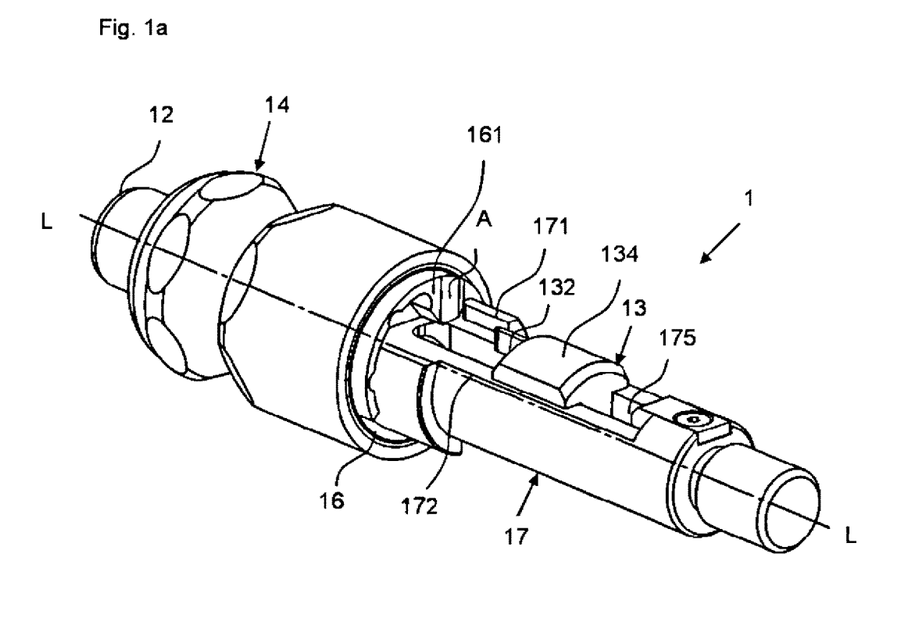
FIG. 1a shows a perspective partial view of the handle with the carriage at its proximal abutment position.

A handle 1 according to the invention is shown in a perspective partial view in FIG. 1a, in which the grip part 15 (see FIG. 7) has been cut away in order to better depict the components under the grip part 15. The handle 1 has an elongate or cylindrical main body 17, which has a cross section varying along its longitudinal axis L. The end of the main body lying at the bottom right of the figure is the proximal end, and the end facing upward to the left is the distal coupling portion 12 on which an (instrument) shaft can be coupled, the latter usually having a jacket tube and an actuation rod 190 (see FIG. 6) guided movably therein.

Figure 6:
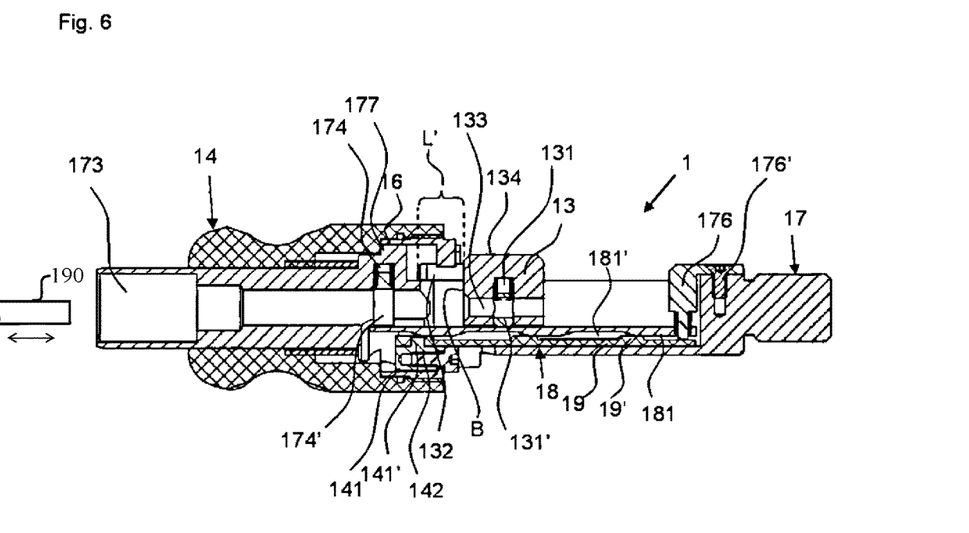
FIG. 6 shows a longitudinal sectional view of part of the handle.

The jacket tube is connected in a stationary manner to the main body 17, while the actuation rod 190 is intended to be connected to the longitudinally axially movable carriage 13. The carriage 13 is guided in a guide groove 175 extending along the longitudinal axis L of the main body 17, and it has a T-shaped cross section, while the drive of the carriage 13 is realized via a movement thread 134 on its jacket surface, which movement thread 134 can be brought into engagement with a rotary wheel 11 as first actuation element 11 (see FIG. 7).

In the area of the guide groove 175, the main body 17 has a flattened part, which is formed by recessing a cylinder segment from the main body 17. This recess or flattened part has a plane surface which serves as a sliding surface 172 for the two branches of the T-shaped carriage 13. From its distal abutment position shown in FIG. 1a, the carriage 13 can be moved to a proximal position, wherein the finger 132, which extends eccentrically with respect to the longitudinal axis of the main body 17 from a front face B (see FIG. 6) of the carriage 13 facing in the distal direction, first comes to bear on a proximal abutment 161. The handle 1 moreover has a second actuation element 14, which is arranged distally adjacent to the rotary wheel 11, which is not shown here (see FIG. 7). The second actuation element 14 has two degrees of freedom of movement: It can be rotated about the longitudinal axis L of the main body 17, and it can be moved along the longitudinal axis. In the position shown, however, the degree of freedom of movement along the longitudinal axis is blocked by the fact that a lug 171 which is arranged stationary on the main body 17, and which has a hook-shaped cross section forming an undercut, provides an abutment. The second actuation element 14 is connected on the inside to a locking ring 16 for conjoint rotation therewith, which locking ring 16 has a radially inwardly facing protuberance 161, which in turn has a locking surface A that bears on the lug 171 in order to lock the longitudinal axial movement.

Figure 1B:
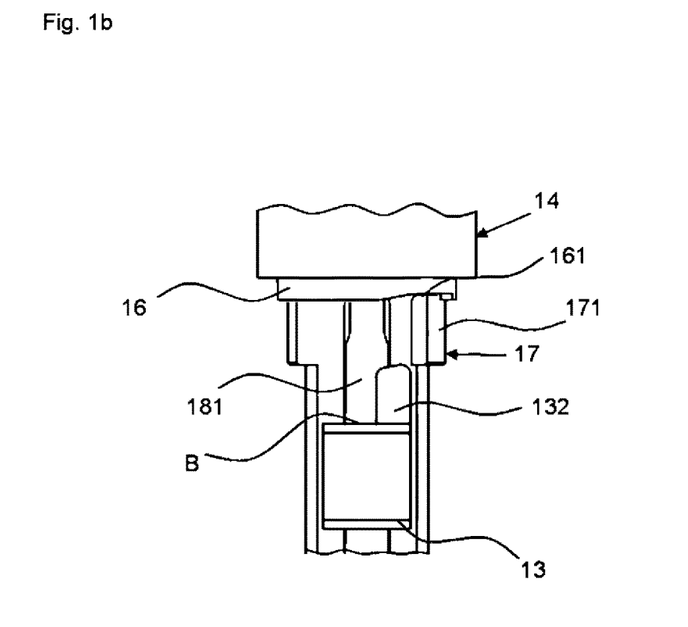
FIG. 1b shows a plan view of part of the handle.

The plan view in FIG. 1b, in a direction perpendicular to the sliding surface 172, shows the area around the proximal end of the second actuation element 14 and the carriage 13, wherein a trigger band 181, which can be seen at the bottom of the guide groove 175, can be moved in a direction out of the drawing plane in order to release the engagement of the actuation rod with the carriage 13, which engagement is realized via a releasable coupling device on that side of the carriage facing away from the view, which can be clearly seen in FIG. 6.

Figure 2A:
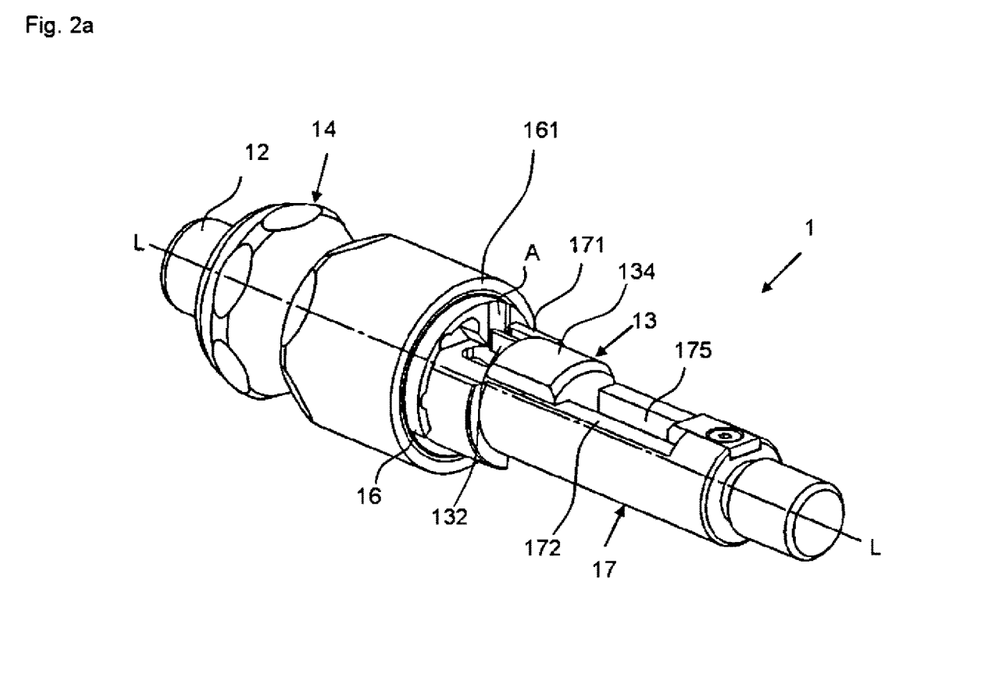
FIG. 2a shows a perspective partial view of the handle with the carriage at its distal abutment position.
Figure 2B:
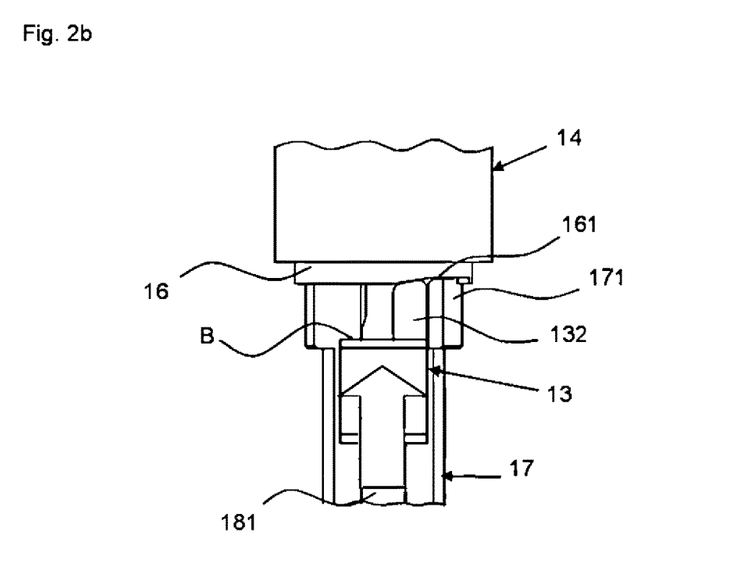
FIG. 2b shows a plan view of part of the handle.

The finger 132 of the carriage 13 and the protuberance are positioned, and matched to each other in terms of their dimensions, in such a way that the finger 132 bears on the protuberance 161 when the carriage 13 is moved to its distal abutment, as is shown in FIG. 2a and FIG. 2b. The surface A of the protuberance 161 of the locking ring 16 blocks the further travel in the distal direction. The travel between the proximal abutment (see FIG. 1a and FIG. 1b) and the distal abutment corresponds to the path that is used in normal mode for operating a surgical tool, for example forceps or scissors, while a travel of the carriage 13 going beyond this remains blocked.

Figure 3A:
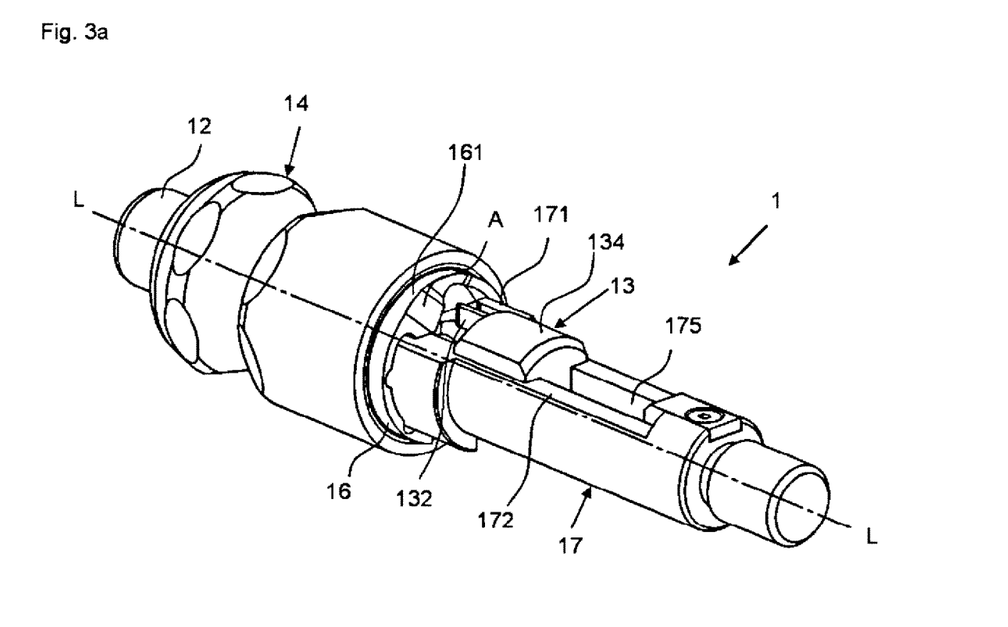
FIG. 3a shows a perspective partial view of the handle with the carriage at its distal abutment position and with the second actuation element in the release state.
Figure 3B:
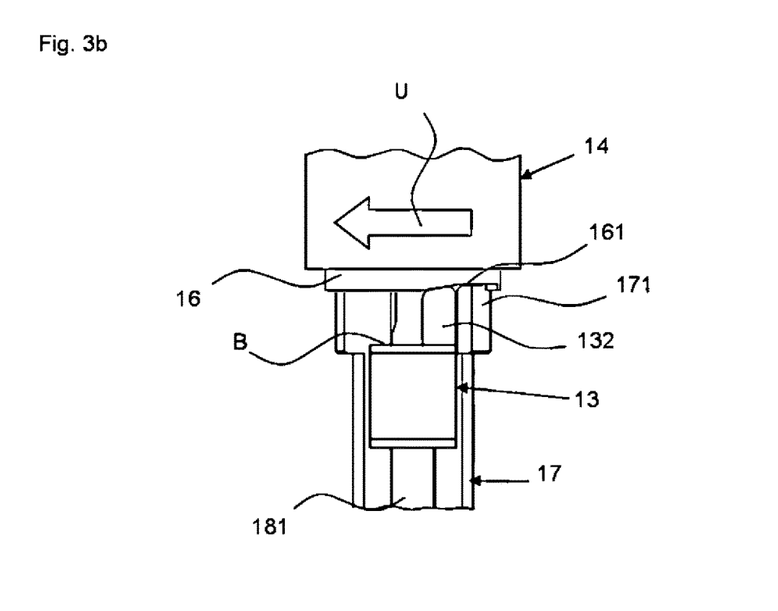
FIG. 3b shows a partial plan view of part of the handle.
Figure 4A:
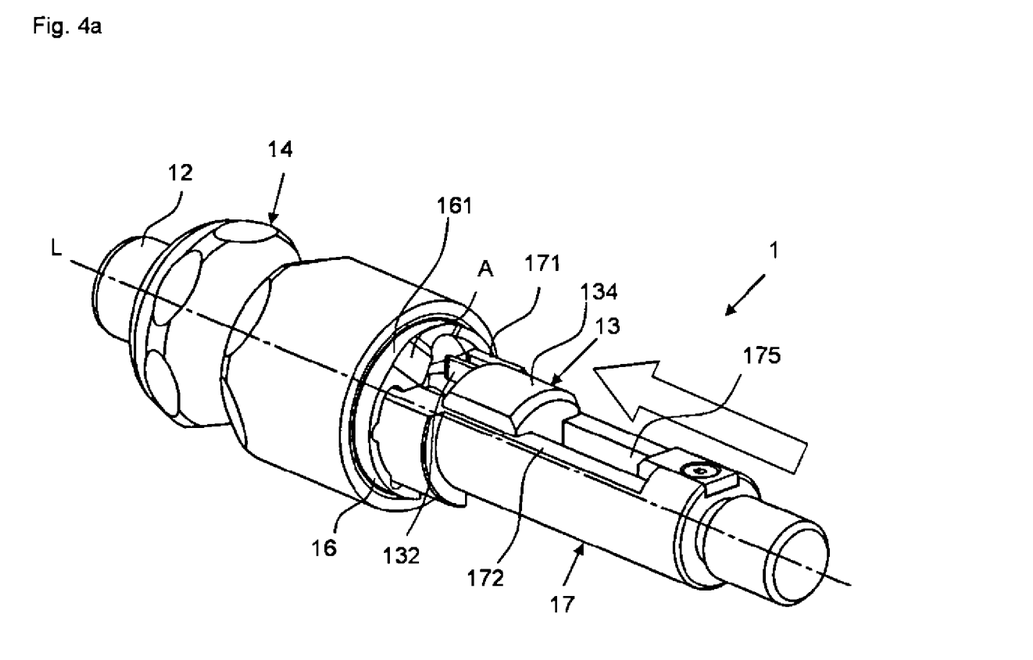
FIG. 4a shows a perspective partial view of the handle with the second actuation element in the release state and with the carriage distally behind its distal abutment position.
Figure 4B:
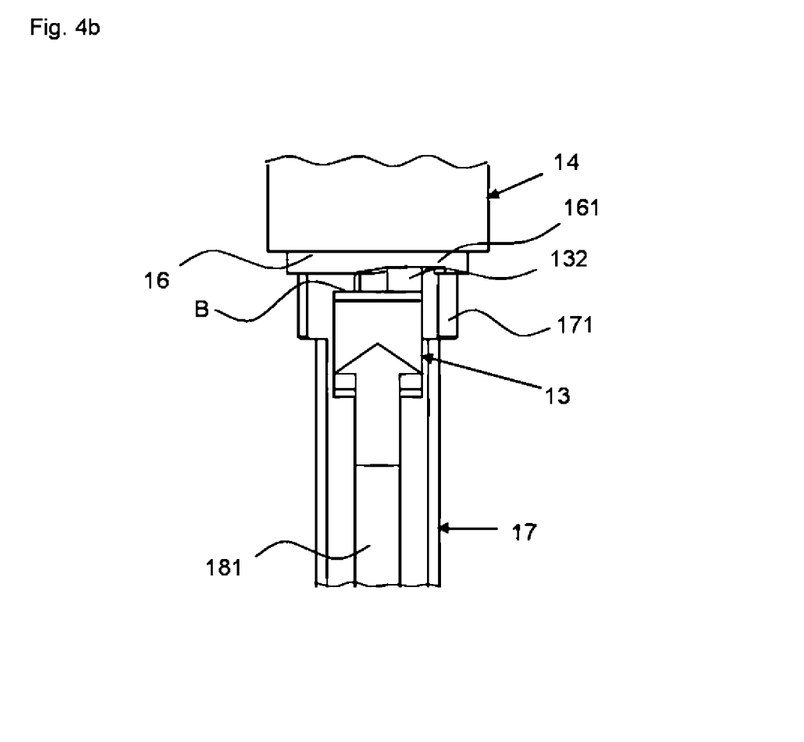
FIG. 4b shows a plan view of part of the handle.

If a further range of travel L' (see FIG. 6) of the carriage 13 in the distal direction is now to be freed, the second actuation element 14 is rotated in the direction of rotation U (toward the left in the drawing), wherein the protuberance 161 of the locking ring is turned together with the second actuation element. The end state of the rotation is shown in FIG. 3a and FIG. 3b. The protuberance 161 then bears on the sliding surface 172 of the portion of the main body 17 with the cylinder-segment-shaped recess and blocks a further rotation to the left. The finger 132 now no longer bears on the protuberance 161 and can be moved farther in the distal direction, until the front face B of the carriage 13 facing the locking ring 16 bears on the end of the guide groove 175. A position of the carriage 13 shortly before the front face B bears on the end of the groove 175 is shown in FIG. 4a and FIG. 4b, wherein the direction of movement of the carriage 13 along the now freed range of travel L' (see FIG. 6) is indicated by an arrow. However, there is still a distance between the locking ring 16 and the front face B of the carriage 13 facing the locking ring 16. The plan view in FIG. 4b additionally shows a bevel of the protuberance 161, which bevel "climbs" proximally in the direction of rotation U (see FIG. 3b) of the second actuation element 14 and of the locking ring. The second actuation element 14 can also be rotated to its release state under a load that is applied by the finger 132 of the locking ring 13 to the protuberance 161 in the locked state (see FIG. 2b) and that leads to a bracing of the locking ring 13, since the bevel, during the rotation to the left, frees a gap between the distal front face A of the finger 132 and the protuberance, as a result of which the bracing is canceled.

Figure 5A:
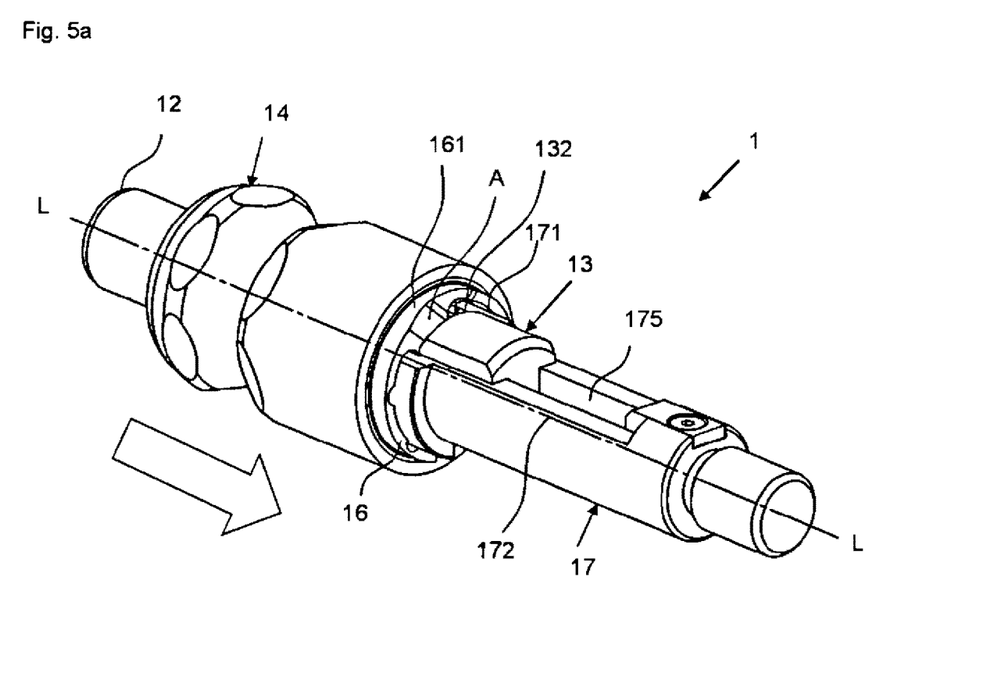
FIG. 5a shows a perspective partial view of the handle with the second actuation element in the release state and with the carriage by the distal range of travel behind its distal abutment position.
Figure 5B:
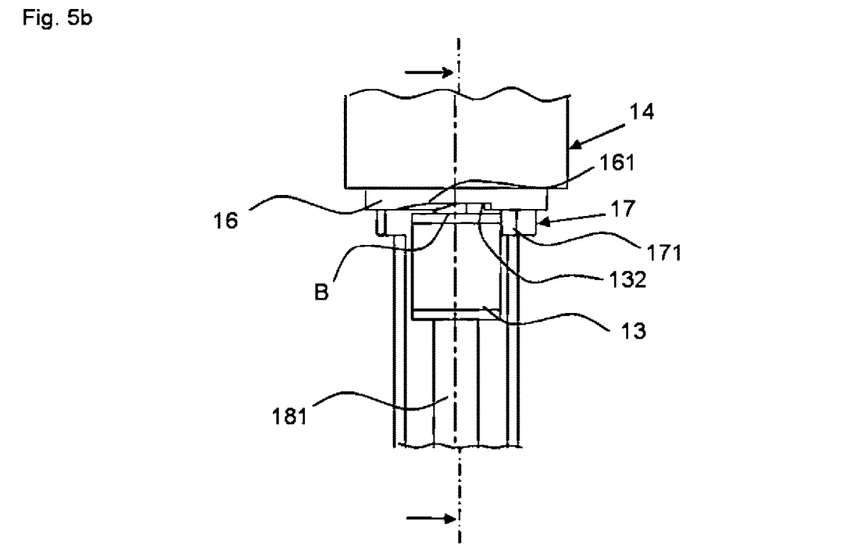
FIG. 5b shows a plan view of part of the handle.

The cross section of the lug 171 is hook-shaped, wherein the transition from the cylindrical main body 17 to the lug 171 is tangential. The outer contour of the cross section of the lug 171 represents a more or less kink-free continuation of the outer contour of the cross section of the main body 17, by which it is made possible that the lug 171, although bearing with a locking action on the protuberance 161 of the locking ring 16 in the locked state of the second actuation element 14, does not touch the locking ring 16 in the release state, as a result of which it is possible to move the second actuation element 14, and with it also the locking ring 16, in the proximal direction beyond the lug 171, which is shown in FIGS. 5a and 5b, where FIG. 5b shows a plan view of the functional position shown in FIG. 5a.

The state of the handle 1, with the finger 132 partially guided distally through the locking ring 16, is also shown in the longitudinal section in FIG. 6. The second actuation element 14 is moved in the proximal direction, wherein an abutment 177 of the main body 17 prevents a further movement of the second actuation element 14 in the proximal direction, i.e. to the right in the figure. The handle 1 is intended to be coupled to a shaft in which an actuation rod 190 is guided movably.

For coupling a jacket tube of the shaft, a receiving bore 173, into which the jacket tube is inserted, is present in the main body 17. The jacket tube is locked to the main body by means of a spring-loaded locking slide 174, while the actuation rod 190 is guided as far as the carriage 13, and in a receiving bore 133 in the carriage 13, and is locked to the carriage 13 by the spring-loaded locking slide 131. The two spring-loaded locking slides 131, 174 can be unlocked by a common trigger device 18, which has a stationary trigger band 181 and a movable trigger band 19. The movable trigger band 19 is connected in a fixed position to the second actuation device 14 and, when the latter is moved in the proximal direction, is moved along with it in the proximal direction. The trigger ribs 19' of the movable trigger band 19 slide on undulating portions 181' of the stationary trigger band 181, wherein a lifting movement perpendicular to the direction of movement is generated that acts on trigger pins 131', 174' of the locking slides 131, 174 of the carriage 13 and of the main body 17 in order to release the locking. The movable trigger band 19 is connected with a form fit to the second actuation element 14 by means of a linking device 141 that carries a linking lug 141', wherein the linking device 141 itself is screwed to the second actuation element 14 (see screw 142). The stationary trigger band 181 is held in position by a securing bracket 176, which is connected to the main body 17 by the screw 176'.

Figure 7:
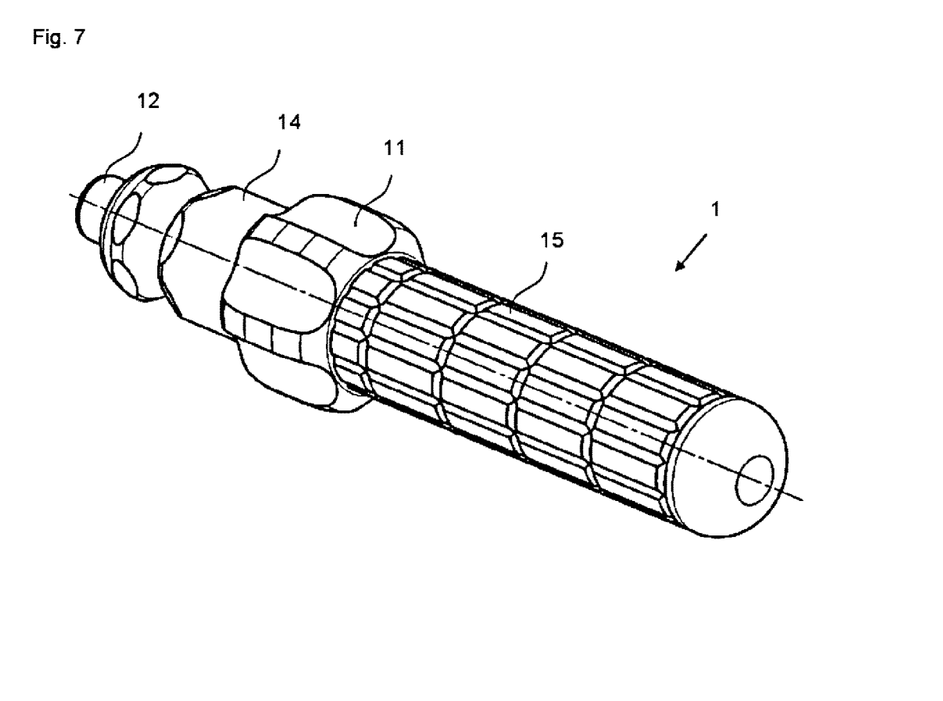
FIG. 7 shows a perspective view of the handle.

In FIG. 7, finally, the complete handle 1 is shown in a perspective view, and the grip part 15, which was cut away in FIG. 1a to FIG. 6, is also shown here. An operator can ergonomically actuate the rotary wheel 11 with his index finger/middle finger and thumb, while the second actuation element 14 in normal operation does not get in the way, since it is arranged in the distal direction from the rotary wheel 11. If the tool mounted on the end of the shaft is to be brought to the beyond open position, the handle 1 can continue to be held by one hand on the grip part 15, while the second actuation element 14 can be rotated using the other hand. Operation with just one hand is also advantageously possible. Separation of the shaft from the handle 1 is also ergonomically possible: The handle 1 is held with one hand on the grip part 15, while the release of the locking of the jacket tube and of the actuation rod of the shaft takes place jointly by pulling back the second actuation element 14.

LIST OF REFERENCE SIGNS 1 handle
11 first actuation element, rotary wheel
12 distal coupling portion
13 movable carriage
131 locking device, locking slide
131' trigger pin
132 finger of the carriage
133 receiving bore of the carriage
134 movement thread of the carriage
14 second actuation element
141 linking device of the movable trigger band
141' linking lug
142 screw connection
15 grip part
16 locking ring
161 protuberance of the locking ring
17 main body
171 lug of the main body
172 sliding surface of the main body
173 receiving bore of the main body
174 locking device of the main body
174' trigger pin
175 guide groove of the main body
176 securing bracket of the trigger band
176' screw
177 abutment of the main body
18 trigger device
181 stationary trigger band
181' wedge-shaped, undulating or beveled portion of the trigger band
19 movable trigger band 19' trigger rib
A front face of finger facing the locking ring
B front face of the carriage
L longitudinal axis of the main body
L' range of travel of the carriage
U direction of rotation of the second actuation element

The invention claimed is:

1. A handle for a surgical instrument, comprising
a distal coupling portion for coupling to a shaft,
an elongate main body, in which a carriage is guided movably along the longitudinal axis between a first end position and a second end position,
a first actuation element, which is operatively coupled to the carriage in order to move the latter axially, wherein the carriage is designed for the longitudinal axial movement of an actuation rod of the shaft of the surgical instrument,
a second actuation element, which is arranged adjacent to the first actuation element on the longitudinal axis and is rotatable about the longitudinal axis of the elongate main body,
the second actuation element is annular, at least at its end directed toward the first actuation element, and carries on its inner circumference a rotationally fixed locking ring whose inner wall has a protuberance facing radially into the locking ring, said protuberance having a surface lying at least partially in the ring plane,
wherein the carriage has a finger which extends, eccentrically with respect to the longitudinal axis of the main body, from a front face of the carriage facing the locking ring,
wherein, in a locked state of the second actuation element, the surface provides a first abutment for the carriage, since the finger comes to bear on the surface,
wherein, in a release state of the second actuation element, the finger, offset with respect to the surface, faces the locking ring and frees a range of travel of the carriage, and
wherein the second actuation element is movable at least along a longitudinal axial portion of the main body.

2. The handle according to claim 1, characterized in that the main body has, on its outer circumference, a lug which is positioned such that, in the locked state of the second actuation element, it bears on the surface of the protuberance of the locking ring and, in the release state of the second actuation element, it is offset with respect to the protuberance,
wherein the lug has a hook-shaped cross section that extends along the outer circumference of the main body, along a portion parallel to the longitudinal axis of the main body,
and/or
the protuberance is beveled in the circumferential direction of the locking ring.

3. The handle according to claim 1, characterized in that the carriage has a coupling device, which is configured to releasably couple to the actuation rod of the shaft, and
the main body has a coupling device, which is configured to releasably couple to a jacket tube of the shaft.

4. The handle according to claim 3, characterized in that the second actuation element is operatively coupled to a trigger device, which extends parallel to the longitudinal axis of the main body and which, in order to release the coupling devices of the main body and of the carriage, is operatively coupled to the coupling devices of the main body and of the carriage,
wherein the trigger device, in the release state of the second actuation element, is movable along the longitudinal axis together with the second actuation element to a trigger position.

5. The handle according to claim 4, characterized in that the trigger device has a first part, which is configured to be entrained with the second actuation element, and a second part, which is stationary with respect to the longitudinal axis of the main body, and
the first part and/or the second part of the trigger device having a trigger band, which has at least one wedge-shaped, undulating or beveled portion in longitudinal section, which contacts a trigger rib of the respective other part.

6. The handle according to claim 1, characterized in that a resetting device is arranged between the second actuation element and the main body, by means of which the second actuation element is reset.

7. The handle according to claim 1, characterized in that the main body has a longitudinal axial guide groove in which the carriage is guided, wherein, at the first abutment of the carriage, there is a distance between the front face of the carriage and an opposite end of the guide groove, the length of which distance is at least as great as half the length of the finger.

8. The handle according to claim 1, characterized in that in an area of the cylindrical main body, a segment is recessed in which a guide groove is present, which segment has a sliding surface for the carriage.

9. The handle according to claim 1, characterized in that, concentrically within the second actuation element, a guide sleeve is arranged stationary with respect to the main body and, at least at an angle position corresponding to the locked state of the second actuation element, has a longitudinal axial guide track in which an engagement means of the second actuation element or of the locking ring is guided.

10. The handle according to claim 1, characterized in that the first actuation element is a rotary wheel, coupled to the carriage via a movement thread or a slotted guide.

11. A surgical instrument having a handle to which is coupled an instrument shaft in which an actuation rod is guided movably along the longitudinal axis,
wherein the actuation rod is coupled to a longitudinally axially movable carriage of the handle, and
wherein the shaft is coupled, at a distal end of the shaft, to a tool head which is configured to be transferred by means of the actuation rod from an open state to a closed state,
characterized in that,
the handle is a handle according to claim 1.

12. A surgical instrument according to claim 11, characterized in that
the shaft has a jacket tube which is releasably coupled to the distal coupling portion of the handle, wherein the jacket tube has a locking groove, which is in engagement with the coupling device of the main body, and/or
the actuation rod has a locking means, which is in engagement with the coupling device of the carriage.

13. An operating method for a surgical instrument having a handle and a tool head which is configured to be transferred to a beyond open position, said method comprising the steps of:
providing the handle which includes:
a distal coupling portion for coupling to a shaft, and
an elongate main body, in which a carriage is guided movably along the longitudinal axis between a first end position and a second end position, a first actuation element, which is operatively coupled to the carriage in order to move the latter axially, wherein the carriage is designed for the longitudinal axial movement of an actuation rod of the shaft of the surgical instrument, a second actuation element, which is arranged adjacent to the first actuation element on the longitudinal axis and is rotatable about the longitudinal axis of the elongate main body, and the second actuation element being annular, at least at its end directed toward the first actuation element, and carries on its inner circumference a rotationally fixed locking ring whose inner wall has a protuberance facing radially into the locking ring, said protuberance having a surface lying at least partially in the ring plane, wherein the carriage has a finger which extends, eccentrically with respect to the longitudinal axis of the main body, from a front face of the carriage facing the locking ring, wherein, in a locked state of the second actuation element, the surface provides a first abutment for the carriage, since the finger comes to bear on the surface, wherein, in a release state of the second actuation element, the finger, offset with respect to the surface, faces the locking ring and frees a range of travel of the carriage, wherein the actuation rod is coupled to the longitudinally axially movable carriage of the handle, and wherein the shaft is coupled, at a distal end of the shaft, to the tool head which is configured to be transferred by means of the actuation rod from an open state to a closed state, rotating the second actuation element of the handle until the protuberance of the locking ring and the finger of the carriage are offset with respect to each other, thereby transferring the second actuation element to the release state, thereby releasing the range of travel of the carriage, actuating the first actuation element, thereby moving the carriage in the direction of the locking ring and moving the finger as far as an end position behind the ring plane, and thereby indirectly transferring the tool head to the beyond open position.

14. A dismantling method for a surgical instrument having a handle to which is coupled an instrument shaft in which an actuation rod is guided movably along the longitudinal axis, the method comprising the steps of:

providing the handle, the handle including:

a distal coupling portion for coupling to a shaft, an elongate main body, in which a carriage is guided movably along the longitudinal axis between a first end position and a second end position, a first actuation element, which is operatively coupled to the carriage in order to move the latter axially, wherein the carriage is designed for the longitudinal axial movement of an actuation rod of the shaft of the surgical instrument, a second actuation element, which is arranged adjacent to the first actuation element on the longitudinal axis and is rotatable about the longitudinal axis of the elongate main body, the second actuation element is annular, at least at its end directed toward the first actuation element, and carries on its inner circumference a rotationally fixed locking ring whose inner wall has a protuberance facing radially into the locking ring, said protuberance having a surface lying at least partially in the ring plane, wherein the carriage has a finger which extends, eccentrically with respect to the longitudinal axis of the main body, from a front face of the carriage facing the locking ring, wherein, in a locked state of the second actuation element, the surface provides a first abutment for the carriage, since the finger comes to bear on the surface, wherein, in a release state of the second actuation element, the finger, offset with respect to the surface, faces the locking ring and frees a range of travel of the carriage, wherein the actuation rod is coupled to the longitudinally axially movable carriage of the handle, wherein the shaft is coupled, at a distal end of the shaft, to a tool head which is configured to be transferred by means of the actuation rod from an open state to a closed state, and wherein the shaft has a jacket tube which is releasably coupled to the distal coupling portion of the handle and which has a locking groove that is in engagement with the coupling device of the main body, and/or the actuation rod has a locking means which is in engagement with the coupling device of the carriage, rotating the second actuation element of the handle until the protuberance of the locking ring and the lug are offset with respect to each other, thereby transferring the second actuation element to the release state, thereby freeing a passage of the locking ring for the lug of the main body of the handle, moving the second actuation element in a direction toward the locking abutment, thereby entraining the trigger device and bringing it to the trigger position, thus generating a lifting movement of the trigger device in a direction perpendicular to the direction of movement of the second actuation element, transmitting the lifting movement of the trigger device to the coupling devices of the carriage and of the main body, thereby actuating the coupling devices and releasing the engagement of the locking means of the jacket tube of the shaft with the coupling device of the main body and of the locking means of the actuation rod of the shaft with the coupling device of the carriage, and jointly separating the jacket tube and the actuation rod from the handle.

15. The handle according to claim 3, wherein the coupling device of the carriage is a locking slide.

16. The handle according to claim 15, wherein the locking slide is a spring-loaded locking slide.

17. The handle according to claim 3, wherein the coupling device of the main body is a locking slide.

18. The handle according to claim 17, wherein the locking slide is a spring-loaded locking slide.

19. The surgical instrument according to claim 12, wherein the locking means of the actuation rod is a locking indent or a circumferential locking groove.

* * * * *

UNITED STATES PATENT AND TRADEMARK OFFICE
CERTIFICATE OF CORRECTION

PATENT NO. : 10,251,632 B2
APPLICATION NO. : 14/618423
DATED : April 9, 2019
INVENTOR(S) : Robin Merz et al.

Page 1 of 1

It is certified that error appears in the above-identified patent and that said Letters Patent is hereby corrected as shown below:

On the Title Page

Column 1, item (73) Assignee:
"Karl Storz GmbH & Co. KG,
Tuttlingen (DE)"

Should read:
--Karl Storz SE & Co. KG,
Tuttlingen (DE)--

Signed and Sealed this
Twenty-eighth Day of May, 2019

Andrei Iancu
*Director of the United States Patent and Trademark Office*